United States Patent [19]
Spielvogel et al.

[11] Patent Number: 5,312,816
[45] Date of Patent: May 17, 1994

[54] METHOD OF COMBATTING OSTEOPOROSIS IN MAMMALIAN SUBJECTS, UTILIZING ORGANIC BORON COMPOUNDS

[75] Inventors: Bernard F. Spielvogel, Raleigh; Anup Sood, Durham; Iris H. Hall, Carrboro, all of N.C.

[73] Assignee: Boron Biologicals, Inc., Raleigh, N.C.

[21] Appl. No.: 121,221

[22] Filed: Sep. 14, 1993

Related U.S. Application Data

[63] Continuation of Ser. No. 759,222, Sep. 13, 1991, abandoned.

[51] Int. Cl.$^5$ .......................... A61K 31/69; C07F 5/02
[52] U.S. Cl. .......................... 514/64; 568/1; 568/2
[58] Field of Search .......................... 514/64; 568/1, 2; 423/227

[56] References Cited

U.S. PATENT DOCUMENTS

| | | | |
|---|---|---|---|
| 4,312,989 | 1/1982 | Spielvogel et al. | 546/13 |
| 4,499,082 | 2/1985 | Shenvi et al. | 514/2 |
| 4,849,220 | 7/1989 | Nielson et al. | 424/659 |

FOREIGN PATENT DOCUMENTS

0425909A2  5/1991  European Pat. Off. .

OTHER PUBLICATIONS

"Anti-Inflammatory Activity of Diazomethylketone and Chloromethylketone Analogs Prepared From N-Tosyl Aminoacids", J. Pharm. Sci. Dec. 1980.
"Anti-Inflammatory Activity of Amine Cyanoboranes, Amine Carboxyboranes, and Related Compounds", J. Phar. Sci., Sep. 1980, pp. 1025-1029.
"Inhibition of the Serine Proteases Leukocyte Elastase, Pancreatic, Cathepsin G, and Chemotrypsin Bipeptide Boronic Acids", J. Bio. Chem. 1984, pp. 15106-15114.
"The Anti-Inflammatory Activity of 5H-Dibenz[C,E]Azepine-5, 7(6H)Dione, 6,7-Dihydro-5H-Dibenz[-C,E]Azepine, N-Benzoylbenzamide and 1H-Benz[-D,E]Isoquinoline-1,3(2H)Dione Derivatives in Rodents", Aceta Pharm. Nord., 1990, 387-400.
"A Preliminary Study on the Anti-Emphysema Drug, 2-Trifluoro-Acetoamidobenzene-Sulfonylfluoride in CF$_1$ Mice", Pharm. Res. Comm. 1987, pp. 69-83.

*Primary Examiner*—Frederick E. Waddell
*Assistant Examiner*—T. J. Criares
*Attorney, Agent, or Firm*—Steven J. Hultquist

[57] ABSTRACT

A method of combatting, e.g., preventing as well as treating, a disease state such as cystic fibrosis, neonatal hypoxemia, pulmonary hypertension, adult respiratory distress syndrome, psoriasis, spondyloarthritis, rheumatoid arthritis, gout, inflammatory bowel disease, myocardial infarctions, and/or osteoporosis in an animal subject, by administering to the animal subject an amount of an organic boron compound which is effective thereagainst. The organic boron compounds usefully employed in the method of the invention include any suitable organic boron-containing compounds, such as Lewis base-boron adducts; a preferred class of organic boron compounds useful in such method includes boron analogs of α-amino acids, and the corresponding amides and esters of such amino acids. A method is also disclosed of inhibiting enzyme activity in in vitro or in vivo systems comprising administering to such system an enzyme-inhibiting amount of an organic boron compound. Further disclosed is a method of reducing hydroxyproline, calcium, and/or inorganic phosphorous in serum and/or urine of an animal subject, by administering to the animal subject an effective amount of an organic boron compound.

12 Claims, No Drawings

METHOD OF COMBATTING OSTEOPOROSIS IN MAMMALIAN SUBJECTS, UTILIZING ORGANIC BORON COMPOUNDS

CROSS REFERENCE TO RELATED APPLICATION

This is a file wrapper continuation of U.S. application Ser. No. 07/759,222 filed Sept. 13, 1991, now abandoned.

BACKGROUND OF THE INVENTION

1. Field of the Invention

The present invention relates to a method for preventing and/or treating osteoporosis and other disease states in animal subjects, utilizing organic boron compounds.

2. Description of the Related Art

The adult skeleton is composed of 80% cortical and 20% trabecular bone. Bone matrix is composed of 25% collagen, 65% inorganio material, and 10% non-cellular proteins (i.e., osteocalcin, silaoprotein, proteoglycans and osteonectin) and lipids. Osteoblasts synthesize and secrete Type 1 collagen and mucopolysaccharides to form the bone matrix which is laid down between the thin layers of osteoid. The layers are subsequently mineralized with 99% of the body's calcium found in the bone as a calcium phosphate complex with hydroxyapatite. Osteoblasts also synthesize and release $Pg-E_2$, osteocalcin, osteonectin, and collagenase. These cells have membrane receptors for PTH, VitD, and glucocorticosteroids.

Osteoclasts are multi-nucleated cells which reabsorb calcium from bone and cartilage. These cells may be derived from hemopoietic stem cells, i.e., mono-nucleated phagocytic cells. These cells lie on the bone surface (Howship's lacunae) and the surface becomes ruffled (motile microvilli). This area is sealed off from the neighboring cells. In these pockets, acid is produced which activates acidic hydrolytic enzymes and neutral proteases are released. Calcium is chelated by organic anions, e.g., citrate.

Osteoblasts release collagenase which removes protein from the surface of the bone, thus allowing the osteoclasts to attach. Collagenase cleaves the native helical molecule of collagen. The other proteolytic enzymes, e.g. neutral and acidic cathepsins, digest the protein further with the release of hydroxyproline to the extracellular compartment, which is an index of bone resorption. Hydroxyapatite protects collagen from denaturation. Collagenase and stromelysin are extracellular calcium dependent, zinc endoproteinases which hydrolyze collagen. Proteoglycan is thought to be a substrate for stromelysin (matrixin, proteoglycanase, transin, and MMP-3). These enzymes exist as zymogens or proenzymes. The proenzymes are activated by organomercurials, serine proteinases, oxidants and surfactants. The amino acid sequences of the metalloproteinases are known from the corresponding cDNA. The activity of the enzyme is inhibited by endogenous tissue inhibitors (TIMP). In humans a collagenase inhibitor has been identified in the alpha-2 macroglobulin fraction of plasma. Previous studies have shown that hydroxamates, thiol analogs, phosphorous-based derivatives, eriochrome, black T and gold inhibit collagenase, HFC activity.

Osteoporosis is generally associated with a reduced trabecular bone volume leading to increased risk of bone fractures. This process is probably due to a metabolic imbalance between the rates of new bone formation and bone resorption. Osteoporosis can be divided into two classes: (1) type I or post-menopausal,which is related to reductions in estrogen content and affects primarily trabecular bone, and (2) type II or senile, which is related to reduced calcium absorption and affects primarily cortical bone.

Bone resorption can be divided into two processes which are probably being carried out concurrently. Phase I involves the inorganic metabolism conducted principally by osteoclasts, macrophages, monocytes, PMNs, and fibroblasts. This process is regulated by PTH, $Pg-E_2$, and cAMP which activate lysosomal hydrolytic enzymes and causes solubilization of the minerals in the bone, releasing calcium to the blood. Phase II involves organic metabolism where there is proteolytic destruction of the bone matrix collagen, releasing hydroxyproline to the blood. This process is initiated by the release of collagenase and cathepsin D from osteoblasts at the bone surface. The cellula enzymes belong to the metalloproteinase group of proteolytic enzymes which usually function at neutral pH. PTH binds to membrane receptors on osteoblasts, pre-osteoblasts and osteocytes, which activates the release of calcium from the dense bone, probably due to the activation of lysosomal enzymes, e.g., cathepsins, cAMP, interleukin-1, or prostaglandins.

In the elderly population there is a decrease of estrogen, progesterone, testosterone and vitamin D3 levels with age. With advanced age there is a reduction of calcitonin which severely reduces calcium absorption from the gut. There is a positive correlation between the extracellular reduction of these physiological parameters and with osteoporosis. Other factors are: smoking, lack of exercise, sunlight, and disease states like myeloma, skeletal metastasis, gastric surgery, anticonvulsant therapy, male hypogonadism, thyrotoxicosis, amenorrhea, anorexia nervosa, hyperprolactinanemia, diabetes mellitus, immobilization, osteogenic imperfecta, and homocystinuria.

A number of agents have been noted to attenuate loss of bone mass in elderly humans or to accelerate bone growth in the young, such as estrogens, insulin, fluorides, anabolic steroids, calcitonin, growth hormone, fibroblast growth factor, transforming growth factor, epidermoid growth factor, bone morphogenic protein (osteogenin), diphosphates, and oral calcium supplements, with varying degrees of success. Most evidence today indicates that massive intakes of calcium (1500–2000 mg/day) orally does not prevent bone loss in post-menopausal women. It is not clear what the mechanism of action of estrogen is in blocking bone resorption. Estrogen therapy increases calcitonin in menopausal women which activates the metabolite of Vit-D3 for calcium absorption from the gut. There may be more receptors in the gut for the absorption of calcium in the presence of estrogen and there is an increase in calcium binding protein. Progesterone probably facilitates calcium flux into bone. Calcitonin acts directly on osteoclasts via cAMP to inhibit bone resorption.

Bone mass is decreased by treatment with the following drugs over a long period of time: glucocorticoids, thyroxine, heparin, cytotoxic drugs, retinoids [vit A], phorbol esters, Pg-E's, interleukin-1, endotoxins and parathyroid hormone (PTH). Apparently PTH stimulates production and relase of cAMP and prostaglandin synthesis which is coupled with the release of collagenase. This causes the osteoblasts to become flattened and fibroblastic in shape. They release chemical substances, Pg-$E_2$, which attract osteoclasts to the surface of the bone. Pg-$E_2$ triggers the release of osteoclasts activating factor. At the surface there is local production of acids and carbonic anhydrase II, an isoenzyme. Inhibition of these metabolic processes also slows the bone resorption process.

At this stage there is an influx of other types of cells, e.g., macrophages, fibroblasts and monocytes which can continue the resorption process. Certain mechanisms in the movement of calcium from blood to bone are known. The metabolite of vitamin D, 1,25(OH)2Vit-D3, induces calcium transport by binding to a specific cytosol/nuclear receptor and forming a complex. This complex binds to chromatin DNA increasing template activity and initiating the synthesis of the calcium binding protein. Corticosteroids are known to suppress prostaglandin synthesis and reduce the levels of osteocalcin (Gla protein, or BGP). This protein stimulates osteoblastic activity.

There are data which suggest that corticosteroids modulate the number of receptors on osteoblasts for 1,25(OH)2Vit-D3, as well as alkaline phosphatase and collagen synthesis. Sodium fluoride stimulates osteoblast function by recruiting an increased number of osteoblasts. There is evidence that fluorapatite crystals form which are more resistant to resorption. Bisphosphonates are inhibitors of crystallization and calciferication of bone. Heparin increases the production of collagenase and enhances its release and activity. Thus there are numerous sites within the regulation of calcium metabolism and proteolytic enzymes where therapeutic agents may function.

Bone resorption appears to be blocked by sulfanilamide, acetazolamide, methazolamide, benzolamide, ethoxzolamide, flurbiprofen and boron. No doubt a number of these agents are inhibiting the carbonic anhydrase enzyme so that hydrogen ions are not generated to produce an acidic medium. Other agents like thiazides inhibit calcium excretion in the urine. Boron depletion depresses growth in chicks when inadequate amounts of cholecalciferol is in the diet. Boron treatment (3.23 mg/day) of postmenopausal women has been shown to result in higher plasma levels of calcium and serum 25-hydroxycholecalciferol and lower levels of calcitonin and osteocalcin. Recent work at the U.S. Department of Agriculture (Grand Forks, N. Dak.) has shown that inorganic boron, e.g., boric acid or sodium borate, in the diet at 3 mg/day blocks the urinary excretion of calcium, magnesium and perhaps phosphorus. Boron supplements markedly elevate estrogen and testosterone levels and supposedly block the process of osteoporosis. Dietary boron is useful in cholecalciferol-deficient chicks to correct cartilage growth.

Unfortunately, the intake of boron in the form of boric acid, or boric acid salts, has a number of undesirable side effects. The intake of boric acid (at dosages of 250 mg/kg for 16 days) has been found to cause severe degeneration of the testes with giant cell formation, pyknosis and exfoliation. Further, such intake of boric acid causes an increase in alkaline phosphatases in tissues, hepatic glycogen content, and maintenance of body fat. Nausea, vomiting, diarrhea, dermatitis, depressed growth, and lethargy occur in adults treated with boron as a trace element, in inorganic forms. Further, the metabolization of boron from such norganic boron compounds is relatively inefficient. Finally, the marked elevation in estrogen and testosterone levels is associated with undesirable side effects in some instances, including mood disorders, water retention, Na+ retention, thromboembolism, endometrial hyperplasma, cholestatic jaundice, headaches, gastrointestinal distress, virilization, and carcinoma of the biliary tract.

Accordingly, it would be a significant advance in the art to provide a method of combatting osteoporosis, which is not subject to the aforementioned deficiencies associated with boric acid and boric acid salts.

It would be particularly desirable to provide a method of combatting osteoporosis, which is bioactive via a non-estrogenic mechanism.

Accordingly, it is an object of the present invention to provide an improved method of combatting osteoporosis, which is free of the aforementioned deficiencies.

It is another object of the present invention to provide a method of combatting osteoporosis utilizing boron in a form taken up by cells more effectively than boric acid or borate salts, and which combats osteoporosis by different mechanisms than the boric acid and boric acid salt compounds used for such purpose in the prior art.

Other objects and advantages of the present invention will be more fully apparent from the ensuing disclosure and appended claims.

SUMMARY OF THE INVENTION

The present invention relates in one aspect to a method of combatting (e.g., preventing as well as treating) osteoporosis in an animal, e.g., mammalian subject, comprising administering to the animal subject an amount of an organic boron compound which is effective against such osteoporosis.

The organic boron compounds usefully employed in the broad practice of the present invention may include any suitable organic boron-containing compounds, such as Lewis base-boron adducts or any other boron-containing organic compounds which are effective to combat osteoporosis, as a preventative thereagainst, or as a treatment agent to ameliorate or reverse osteoporosis.

The organic boron compounds employed in the practice of the present invention may for example comprise at least one organic boron compound selected from the following classes:

Class 1: organic boron compounds of the formula:

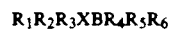

$$R_1R_2R_3XBR_4R_5R_6$$

wherein:

X is N or P;

$R_1$, $R_2$, $R_3$ are independently selected from H, $C_1$–$C_{20}$ linear or branched alkyl, alkoxy, alkylaryl, aryl, and substituted aryl, or $R_1$, $R_2$, and $R_4$ together with X form a heterocyclic ring structure, with the proviso that when X=N, $R_1$, $R_2$ and $R_3$ are not alkoxy;

$R_4$ and $R_5$ are independently selected from H, $C_1$–$C_{20}$ linear or branched alkyl, aryl, alkylaryl, and substituted aryl;

$R_6$ is H, $C_1$–$C_{20}$ linear or branched alkyl, aryl, alkylaryl, substituted aryl, CN, COOH, COOM, COOR$_7$, CONHR$_7$, CONHOH, COAA, or $R_4$, $R_5$, and $R_6$ together with B form a heterocyclic ring structure;

where:

M is Li, Na, K, or ammonium ion;

$R_7$ is H, $C_1$–$C_{10}$ alkyl, substituted alkyl, aryl, or substituted aryl; and AA is NHCH ($R_8$) COOR$_9$ or NHCH ($R_8$) CONHR$_9$ where $R_8$ is selected from the side chain of common amino acids and $R_9$ is H, or $C_1$–$C_5$ alkyl.

Class 2: organic boron compounds of the formula:

$R_1R_2R_3XBR_4$ $(R_5)_2$ wherein: $R_1$, $R_2$, $R_3$, $R_4$ and X are same as above, and $R_5$ is CN.

Class 3: organic boron compounds of the formula:

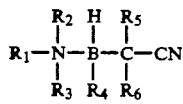

wherein:

$R_1$, $R_2$ and $R_3$ are same as in Class 1;

$R_4$ is H, $C_1$–$C_{10}$ linear or branched alkyl, alkylaryl, or aryl; and $R_5$ and $R_6$ are independently selected from H, $C_1$–$C_{10}$ alkyl, alkylaryl, aryl, or substituted aryl.

Class 4: organic boron compounds of the formula:

$(R_1O)_2PCH_2NR_2R_3BHR_4R_5$ wherein:

$R_1$ is $C_1$–$C_{10}$ linear or branched alkyl, alkylaryl, or aryl;

$R_2$, $R_3$ are independently selected from H, and $C_1$–$C_{10}$ linear or branched alkyl;

$R_4$ is H, $C_1$–$C_{10}$ linear or branched alkyl, alkylaryl, or aryl;

$R_5$ is CN, COOH, CONHR$_6$, COOR$_6$, wherein $R_6$ is same as $R_7$ in Class 1.

Class 5: organic boron compounds of the formula:

$R_1R_2R_3BNCH_2CH_2XCR_4$ wherein:

X is O or S;

$R_1$, $R_2$, $R_3$ are independently selected from H, $C_1$–$C_{10}$ alkyl, alkylaryl, and aryl;

$R_4$ is NMe$_2$ or $R_5$, wherein $R_5$ is $C_1$–$C_{10}$ linear or branched alkyl, alkylaryl, aryl, or substituted aryl.

Class 6: organic boron compounds of the formula:

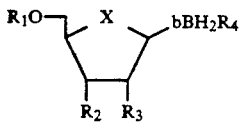

wherein:

X is C or O;

$R_1$ is H or a suitable protecting group, preferably trialkylsilyl, benzoyl, or acetyl;

$R_2$ is H or OH;

$R_3$ is H or OH;

b represents a nucleoside base, preferably with the BH$_2$R$_4$ group is bonded to a base nitrogen atom of the nucleoside base;

$R_4$ is CN, COOH, COOR$_5$, or CONHR$_5$, wherein $R_5$ is H, $C_1$–$C_{10}$ alkyl, alkylaryl, aryl, or substituted aryl.

Class 7: organic boron compounds of the formula:

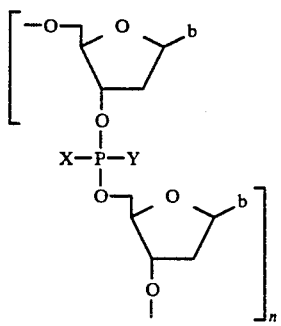

wherein:

n = 1–50, preferably 1–40, and most preferably 1–25;

b is a nucleoside base;

X is O, or OR (where R=CH$_3$, CH$_2$CH$_2$CN, or CH$_2$CH$_3$); and

Y is BH$_3$, BH$_2$CN, BH$_2$COOH, BH$_2$COOR$_1$, or BH$_2$CONHR, wherein $R_1$ is H, or $C_1$–$C_5$ alkyl.

Class 8: metal complexes of amine-cyanoboranes and amine-carboxyboranes.

A preferred class of organic boron compounds having utility in combatting osteoporosis in the broad scope of the present invention are the organic boron compounds which (1) effect inhibition of enzymes which are directly or indirectly involved in mediating osteoporosis, such as trypsin, collagenase, 5'-lipoxygenase, cyclooxygenase, elastase, etc., and (2) preferably also inhibit prostaglandin synthetase activity. These respective enzymes (trypsin, collagenase, elastase, prostaglandin synthetase, etc.) appear to favor bone resorption and can therefore create a metabolic imbalance favoring the development and progression of osteoporosis.

A particularly preferred class of organic boron compounds useful in the practice of the present invention includes Class 1 compounds of the formula $R_1R_2R_3NB(H)R_4COOH$, which are boron analogs of α-amino acids, and are isoelectronic and isostructural with the α-amino acids. The α-carbon in such compounds is replaced by boron. Corresponding amides and esters of such α-amino acids may also be usefully employed in the practice of the invention.

The carboxyborane adducts of amines, and corresponding esters and amides, are boron analogs of the amino acids that affect bone formation and/or resorption. These adducts exhibit particularly useful activity for anti-osteoporosis applications.

In another aspect, the present invention relates to a method of inhibiting enzyme activity in an animal subject attributable to at least one enzyme selected from the group consisting of collagenase, prostaglandin synthetase, acidic phosphatase, aryl sulfatase, 5'-lipoxgyenase, and prostaglandin cyclooxygenase, comprising administering to the animal subject an enzyme-inhibitingly effective amount of an organic boron compound effective against such at least one enzyme.

In a further aspect, the present invention relates to a method of combatting in an animal subject a disease state selected from the group consisting of osteoporosis, cystic fibrosis, neonatal hypoxemia, pulmonary hypertension, adult respiratory distress syndrome, psoriasis, spondyloarthritis, rheumatoid arthritis, gout, inflammatory bowel disease, myocardial infarctions, and combinations thereof, comprising administering to the animal subject a disease-combatting amount of an organic boron compound effective for combatting such disease state.

As used herein, the term "compound", in reference to organic boron compounds usefully employed in the practice of invention, is intended to be broadly construed to include compounds per se, as well as adducts, complexes, etc., which contain (1) boron in a therapeutic and bioavailable form, and (2) an organic moiety or moieties. Such "compounds" may be covalently, ionically, and/or otherwise associatively bonded, as regards the constituents thereof.

Other aspects and features of the invention will be more fully apparent from the ensuing disclosure and appended claims.

DETAILED DESCRIPTION OF THE INVENTION, AND PREFERRED EMBODIMENTS THEREOF

The present invention is based on the surprising and unexpected discovery that organic boron compounds may be employed (1) to combat osteoporosis as well as other disease states, e.g., cystic fibrosis, neonatal hypoxemia, pulmonary hypertension, adult respiratory distress syndrome, psoriasis, spondyloarthritis, rheumatoid arthritis, gout, inflammatory bowel disease, and myocardial infarctions, and/or (2) to inhibit enzyme activity of enzymes such as collagenase, aryl sulfatase, 5'-lipoxygenase, prostaglandin cyclooxygenase, and combinations thereof, when effective amounts of organic boron compounds are administered to an animal subject, e.g., mammalian subject.

Organic boron compounds have been found to be taken up by cells far more effectively than inorganic boron compounds, e.g., boric acid or boron salts such as sodium borate. Further, organic boron compounds have been discovered to be usefully employed without stimulating excess production of hormones such as estrogen and testosterone, thereby avoiding side effects and deficiencies associated with inorganic boron compounds. In addition, the organic boron compounds are easier to deliver to the metabolically effective locus, and in many cases are also associated with therapeutic benefits not present when inorganic boron compounds are employed, e.g., anti-inflammatory, anti-tumor, and anti-hyperlipidemic benefits.

The pronounced benefits available from the use of organic boron compounds in accordance with the present invention are truly unexpected in view of the many and severe deficiencies attending the administration of inorganic boron compounds. Such deficiencies of administering inorganic boron compounds to animal subjects include (1) marked elevation of estrogen and testosterone levels, with accompanying increased risk of cancer and hypertension, (2) severe degeneration of the testes with giant cell formation, pyknosis, and exfoliation, (3) nausea, (4) vomiting, (5) diarrhea, (6) dermatitis, (7) depressed growth, and (8) lethargy. Based on these substantial and undesired direct effects and side effects, as associated with administration of boron to animal subjects in inorganic forms, e.g., as boric acid or boric acid salts, it would be expected that organic boron compounds would effect the same deleterious results. This, fortunately and suprisingly, has not been the case.

The organic boron compounds which may be employed in the broad practice of the present invention include any suitable boron-containing organic compounds, preferably Lewis base-boron adducts.

Organic boron compounds which have potential utility in the practice of the present invention include, but are not limited to: the amine-borane compounds disclosed in U.S. Pat. Nos. 4,312,989 and 4,368,194; the ammonia-cyanoborane, sodium iodide complexes disclosed in U.S. Pat. No. 4,209,510; the carboxyborane compounds described in U.S. Pat. No. 4,550,186; the amine carbamoylborane adducts described in U.S. Pat. No. 4,587,359; the amine-carboxyborane compounds described in U.S. Pat. No. 4,855,493; the boron analogs of amino acids described in U.S. Pat. No. 4,647,555; the boron dipeptide compounds disclosed in U.S. Pat. No. 4,977,268; the amine-alkylborane derivatives disclosed in U.S. application Ser. No. 364,650 filed Jun. 9 1989; the phosphite-borane compounds disclosed in U.S. Pat. No. 5,143,907; organic boron compounds described in "Anti-Inflammatory Activity of Amine Cyanoboranes, Amine Carboxyboranes, and Related Compounds" Hall, I. H. et al, J. Pharm. Sci., Vol. 69, No. 9, Sept., 1980, pp. 1025–1029; and organic boron compounds disclosed in "Organoborane Chemistry", by Thomas Onak, Academic Press, New York, N.Y., 1975.

By way of illustration, the organic boron compounds potentially usefully employed in the broad practice of the invention may include boron-containing organic compounds selected from the following classes:

Class 1: organic boron compounds of the formula:

wherein

X is N or P;

$R_1$, $R_2$, $R_3$ are independently selected from H, $C_1$–$C_{20}$ linear or branched alkyl, alkoxy, alkylaryl, aryl, and substituted aryl, or $R_1$, $R_2$, and $R_3$ together with X form a heterocyclic ring structure, with the proviso that when X=N, $R_1$, $R_2$ and $R_3$ are not alkoxy;

$R_4$ and $R_5$ are indepently selected from H, $C_1$–$C_{20}$ linear or branched alkyl, aryl, alkylaryl, and substituted aryl;

$R_6$ is H, $C_1$–$C_{20}$ linear or branched alkyl, aryl, alkylaryl, substituted aryl, CN, COOH, COOM, $COOR_7$, $CONHR_7$, CONHOH, COAA, or $R_4$, $R_5$, and $R_6$ together with B form a heterocyclic ring structure;

where:

M is Li, Na, K, or ammonium ion;

$R_7$ is H, $C_1$–$C_{10}$ alkyl, substituted alkyl, aryl, or substituted aryl; and AA is NHCH ($R_8$) $COOR_9$ or NHCH ($R_8$) $CONHR_9$ where $R_8$ is selected from the side chain of common amino acids and $R_9$ is H, or $C_1$–$C_5$ alkyl.

Class 2: organic boron compounds of the formula:

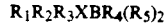

wherein: $R_1$, $R_2$, $R_3$, $R_4$ and X are same as above, and $R_5$ is CN.

Class 3: organic boron compounds of the formula:

wherein:
$R_1$, $R_2$ and $R_3$ are same as in Class 1;
$R_4$ is H, $C_1$–$C_{10}$ linear or branched alkyl, alkylaryl, or aryl; and
$R_5$ and $R_6$ are independently selected from H, $C_1$–$C_{10}$ alkyl, alkylaryl, aryl, or substituted aryl.

Class 4: organic boron compounds of the formula:

wherein:
$R_1$ is $C_1$–$C_{10}$ linear or branched alkyl, alkylaryl, or aryl;
$R_2$, $R_3$ are independently selected from H, and $C_1$–$C_{10}$ linear or branched alkyl;
$R_4$ is H, $C_1$–$C_{10}$ linear or branched alkyl, alkylaryl, or aryl;
$R_5$ is CN, COOH, $CONHR_6$, $COOR_6$, wherein $R_6$ is same as $R_7$ in Class 1.

Class 5: organic boron compounds of the formula:

wherein:
X is O or S;
$R_1$, $R_2$, $R_3$ are independently selected from H, $C_1$–$C_{10}$ alkyl, alkylaryl, and aryl;
$R_4$ is $NMe_2$ or $R_5$, wherein $R_5$ is $C_1$–$C_{10}$ linear or branched alkyl, alkylaryl, aryl, or substituted aryl.

Class 6: organic boron compounds of the formula:

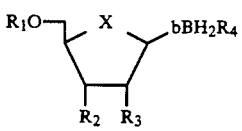

wherein:
X is C or O;
$R_1$ is H or a suitable protecting group, preferably trialkylsilyl, benzoyl, or acetyl;
$R_2$ is H or OH,
$R_3$ is H or OH;
b represents a nucleoside base, wherein the $BH_2R_4$ group preferably is attached to a base nitrogen of the nucleoside base;
$R_4$ is CN, COOH, $COOR_5$, or $CONHR_5$, wherein $R_5$ is H, $C_1$–$C_{10}$ alkyl, alkylaryl, aryl, or substituted aryl.

Class 7: organic boron compounds of the formula:

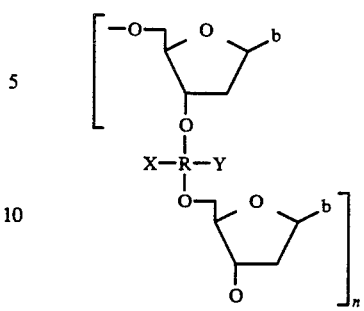

wherein:
n=1–50, preferably 1–40, and most preferably 1–25;
b is a nucleoside base;
X is O, or OR (where R=$CH_3$, $CH_2CH_2CN$, or $CH_2CH_3$); and
Y is $BH_3$, $BH_2CN$, $BH_2COOH$, $BH_2COOR_1$, or $BH_2CONHR$,
wherein $R_1$ is H, or $C_1$–$C_5$ alkyl.

Class 8: metal complxes of amine-cyanoboranes and amine-carboxyboranes.

A particularly preferred class of organic boron compounds from the above-described classes comprises the Class 1 compounds, particularly those in which X is N, viz., the organic boron compounds of the formula:

$R_1R_2R_3NBR_4R_5R_6$

These compounds include amine-carboxyboranes which are boron analogs of α-amino acids. As a result of their structural similarity to such α-amino acids, these compounds evidence a particularly high degree of biocompatability (e.g., metabolic assimilatability, efficiency of metabolic uptake, and deliverability).

In general, the organic boron compounds employed in the method of the invention are readily bioassimilated in an effective and efficient manner, and are more easily deliverable in corporeal systems than are the inorganic boron compounds previously employed for osteoporosis treatment, viz., boric acid and boric acid salts. In addition, the organic boron compounds of the present invention combat osteoporosis and other disease states mentioned hereinabove, as well as effectively suppress certain enzymes which may be implicated in the causation and/or development of such disease states, via metabolic paths which do not effect excessive production of hormones such as estrogen and testosterone. As a result, the use of organic boron compounds in the method of the invention avoids the deficiencies of the prior art use of inorganic boron compounds.

While we do not wish to be bound by any theory or particular mechanism as regards the surprising and unexpected benefits of using organic boron compounds as anti-osteoporosis agents and/or agents for combatting other disease states, there is evidence that such efficacy is the result of inhibition of proteolytic enzymes and other enzymatic and proteinaceous species associated with the causative and developmental mechanisms of osteoporosis and the other mentioned disease states.

The organic boron compounds which are utilized in the method of the present invention may combat osteoporosis by opposing bone resorption processes which create an imbalance between bone formation and resorption. Such osteoporosis-combatting agents may effect such benefit by inhibiting either the inorganic phase resorption processes or organic resorption processes. The inorganic phase of bone resorption includes cell-mediated solubilization of minerals such as $Ca^{++}$, as conducted by lysosomal acidic enzymes of osteoclasts, macrophages, monocytes, PMNs and fibroblasts. Such mineral solubilization process is stimulated by PTH, Pg-$E_2$, and cAMP. The organic phase of bone resorption encompasses the proteolytic destruction of matrix collagen with hydroxyproline release from the bone. Such proteolytic destruction is conducted by collagenase of the osteoblasts, and by lysosomal proteoases, such as cathepsin D, causing degradation of osteoid and lamina bone.

In this respect, the method of the present invention represents an effective approach to combatting osteoporosis and/or the other mentioned disease states, both from the standpoint of prophylactic efficacy of such method as well as its efficacy in respect of ameliorating or even reversing osteoporosis and/or such other disease states already in development.

Illustrative of organic boron compounds which may find utility in the broad practice of the present invention are the following specific boron-containing organic compounds:

(1) Trimethylamine-borane
(2) t-Butylamine-borane
(3) Dimethylamine-borane
(4) Morpholine-borane
(5) Diethylamine-borane
(6) Pyridine-borane
(7) Triphenylphosphine-borane
(8) Ammonia-borane
(9) Ammonia-cyanoborane
(10) Methylamine-cyanoborane
(11) Dimethylamine-cyanoborane
(12) Trimethylamine-cyanoborane
(13) Triphenylphosphine-cyanoborane
(14) Triethylphosphite-cyanoborane
(15) 2'-Deoxycytidine-N3-cyanoborane
(16) 2'-Deoxyadenosine-N1-cyanoborane
(17) N-methylmorpholine-cyanoborane
(18) Ethylenediamine-bis(cyanoborane)
(19) N,N,N',N'-Tetramethylethylenediamine-bis(cyanoborane)
(20) Morpholine-carboxyborane
(21) Triphenylphosphine-carboxyborane
(22) Trimethylamine-carboxyborane
(23) Ammonia-carboxyborane
(24) Triethylphosphite-carboxyborane
(25) N,N-Dimethyloctadecylamine-carboxyborane
(26) N,N-Dimethylhexadecylamine-carboxyborane
(27) Trimethylamine-carboethoxyborane
(28) Trimethylamine-carbomethoxyborane
(29) Trimethylamine-carbobenzoxyborane
(30) Methylamine-carbomethoxyborane
(31) Dimethylamine-carbomethoxyborane
(32) Ammonia-carbomethoxyborane
(33) N,N-Dimethylhexadecylamine-carbomethoxyborane
(34) N,N-Dimethyloctadecylamine-carbomethoxyborane
(35) Ammonia-N-ethylcarbamoylborane
(36) Methylamine-N-ethylcarbamoylborane
(37) Dimethylamine-N-ethylcarbamoylborane
(38) Trimethylamine-N-ethylcarbamoylborane
(39) Trimethylamine-N-propylcarbamoylborane
(40) Trimethylamine-N-phenylcarbamoylborane
(41) Trimethylamine-N-octylcarbamoylborane
(42) 2-(Acetoxy)ethyldimethylamine-borane
(43) 2-(Thioacetoxy)ethyldimethylamine-borane
(44) 2-(Hydroxy)ethyldimethylamine-borane
(45) Diethyl((N,N-Dimethylamine)methyl)phosphonate-N-cyanoborane
(46) Trimethylamine-methyldicyanoborane
(47) Trimethylamine-isopropyldicyanoborane
(48) Trimethylamine-boranecarbohydroxamic acid tetraphenylborate salt.
(49) [(Trimethylamine-boryl)carbonyl]glycine methyl ester
(50) [(Trimethylamine-boryl)carbonyl]phenylalanine methyl ester
(51) [(Trimethylamine-boryl)carbonyl]tyrosine methyl ester
(52) [(Trimethylamine-boryl)carbonyl]serine methyl ester
(53) [(Trimethylamine-boryl)carbonyl]methionine methyl ester
(54) [(Ammonia-boryl)carbonyl]valine methyl ester
(55) [(Ammonia-boryl)carbonyl]isoleucine methyl ester
(56) [(Ammonia-boryl)carbonyl]leucine amide
(57) Pyridine-carboxyborane
(58) N-Methylpyridine-carboxyborane
(59) N-Cyanopyridine-carboxyborane
(60) Trimethylamine-cyanomethylborane
(61) Trimethylamine-2-cyanoisopropylborane
(62) Trimethylamine-α-cyanobenzylborane
(63) Trimethylamine-carboxyborane, sodium salt
(64) Dimethylamine-carboxyborane, sodium salt In general, carboxyborane adducts of Lewis bases (e.g., boron analogs of α-amino acids) and amide and ester derivatives thereof are a preferred class of organic boron compounds in the practice of the present invention, and metal complexes of such Lewis base-carboxyborane adducts and their amide and ester derivatives may also be usefully employed. Illustrative examples of such compounds and complexes are set out below:

$(CH_3)_2N(C_{16}H_{33})BH_2COOH$
$Ph_3PBH_2COOH$
$(CH_3)_2N(C_{18}H_{37})BH_2COOH$
$CH_3NH_2BH_2COOH$
$CH_3NH_2BH_2COOCH_3$
$(CH_3)_3NBH_2COOCH_3$
$CH_3CH_2NH_2BH_2COOH$
$(CH_3)_2NHBH_2COOCH_3$
$Na_2BH_3COO$
$Na(CH_3)_3NBH_2COO \cdot 0.25CH_3OH$
$Na(CH_3)_2NHBH_2COO \cdot 0.45H_2O$
$[Fe_3O((CH_3)_3NBH_2COO)_6(CH_3OH)_3]NO_3 \cdot CH_3CN$
$[Fe_3O((CH_3)_3NBH_2COO)_6(H_2O)_3]Cl$
$[Cr_3O((CH_3)_3NBH_2COO)_6H_2O]NO_3 \cdot CH_3OH \cdot CH_3CN$
Cis-$[Co(en)_2((CH_3NBH_2COO)_2]Cl \cdot 2.5H_2O \cdot 0.5CH_3OH$
$Ca((CH_3)_3NBH_2COO)NO_3 \cdot CH_3COCH_3 \cdot 0.5H_2O$ The organic boron compounds usefully employed in the broad practice of the present invention may be readily synthesized by known and conventional synthesis techniques.

In some instances, it may be desirable to synthesize Lewis base-carboxyborane adducts having a very hydrophobic Lewis base portion of the molecule. Such hydrophobicity may be important for purposes of achieving suitable bioactivity and for enhancing the cellular uptake of the compound.

A bulky Lewis base portion of the molecule may also enhance activity, by obtaining a better steric fit with the active centers of enzymes that are inhibited in the action of the anti-osteoporosis or other disease-combatting agent. Depending on the enzymes responsible for the onset and progression of osteoporosis in the animal (mammalian) subject, it may be desirable to correspondingly size the Lewis base portion of the organic boron compound so as to effectively occupy the active sites of such enzymes. In addition, it may be desirable in some instances to utilize an anti-osteoporosis agent including a multiplicity of Lewis base boron adducts, e.g., carboxyborane compounds, having differently-sized Lewis based moieties in the respective compounds, e.g., alkylamine boron compounds with different alkyl groups associated therewith, as for example methyl, n-propyl, and branched alkyl groups.

Base exchange reactions may be employed for synthesis of such boron compounds having selected Lewis base moieties:

Amine-BH$_2$COOH + Amine′ → Amine′-BH$_2$COOH- + Amine

Alternatively, such Lewis base carboxyborane compounds may be formed, in the case of tertiary amines or phosphines, by intermediate formation of Lewis base-cyanoborane adducts, as shown below:

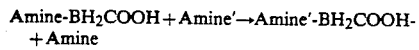

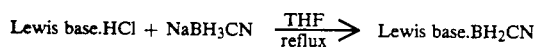

Derivatives of carboxyboranes, e.g., amides (including peptides) and esters can be readily prepared via several known methods, such as amine exchange and from amine-cyanoboranes, as shown in the reaction scheme set out below:

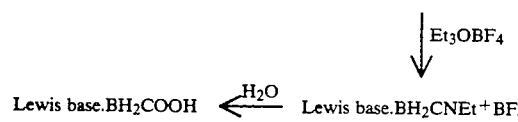

or such derivatives of carboxyboranes may be synthesized directly from amine-carboxyboranes as shown in the reaction scheme below:

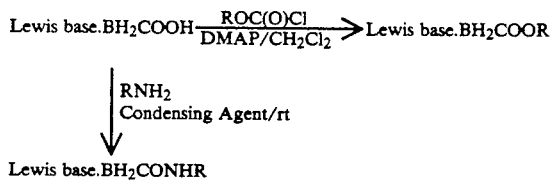

Boronated nucleosides usefully employed as organic boron compounds in the practice of the present invention may suitably be formed as shown below:

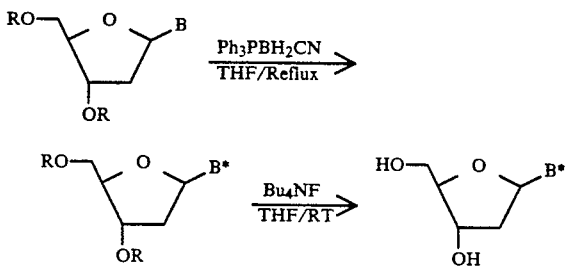

wherein:
R = Si (CH(CH$_3$)$_2$)$_3$;
B = Gua (a), Ino (b), Ade (c), Cyt (d) or Thy (e); and

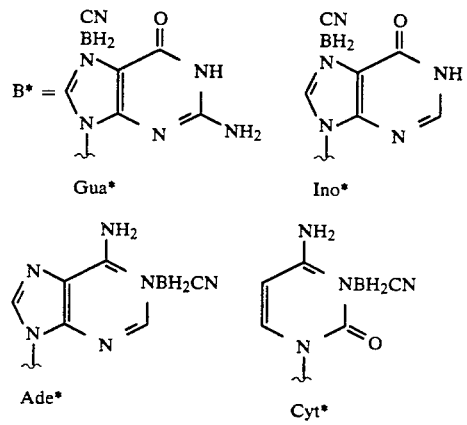

Illustrative nucleoside and nucleoside compounds are specified in Tables A and B below:

TABLE A

STRUCTURE OF NUCLEOSIDE COMPOUNDS

| Compound Reference No. | Deoxyribose 3′ | Deoxyribose 5′ | N$_1$ | Nucleoside Base N$_3$ | N$_7$ |
|---|---|---|---|---|---|
| 29. Ino | OSi(CH(CH$_3$)$_2$)$_3$ | OSi(CH(CH$_3$)$_2$)$_3$ | H | — | — |
| 30. Ino | OH | OH | H | — | BH$_2$CN |
| 31. Ino | OSi(CH(CH$_3$)$_2$)$_3$ | OSi(CH(CH$_3$)$_2$)$_3$ | H | — | BH$_2$CN |
| 32. Gua | OSi(CH(CH$_3$)$_2$)$_3$ | OSi(CH(CH$_3$)$_2$)$_3$ | H | — | — |
| 33. Gua | OH | OH | H | — | BH$_2$CN |
| 34. Gua | OSi(CH(CH$_3$)$_2$)$_3$ | OSi(CH(CH$_3$)$_2$)$_3$ | H | — | BH$_2$CN |
| 35. Ade | OSi(CH(CH$_3$)$_2$)$_3$ | OSi(CH(CH$_3$)$_2$)$_3$ | H | — | — |
| 36. Ade | OH | OH | BH$_2$CN | — | — |
| 37. Ade | OSi(CH(CH$_3$)$_2$)$_3$ | OSi(CH(CH$_3$)$_2$)$_3$ | BH$_2$CN | — | — |
| 38. Cyt | OSi(CH(CH$_3$)$_2$)$_3$ | OSi(CH(CH$_3$)$_2$)$_3$ | — | N$_3$ | — |
| 39. Cyt | OH | OH | — | BH$_2$CN | — |
| 40. Cyt | OSi(CH(CH$_3$)$_2$)$_3$ | OSi(CH(CH$_3$)$_2$)$_3$ | — | BH$_2$CN | — |
| 41. Cyt | H | OSi(CH(CH$_3$)$_2$)$_3$ | — | — | — |

TABLE A-continued

STRUCTURE OF NUCLEOSIDE COMPOUNDS

| Compound Reference No. | Deoxyribose 3' | Deoxyribose 5' | $N_1$ | Nucleoside Base $N_3$ | $N_7$ |
|---|---|---|---|---|---|
| 42. Cyto | H | $OSi(CH(CH_3)_2)_3$ | — | $BH_2CN$ | — |
| 43. T | —O—C(O)CH$_3$ | PH$_3$PBH$_2$C(O)O | — | — | — |

TABLE B

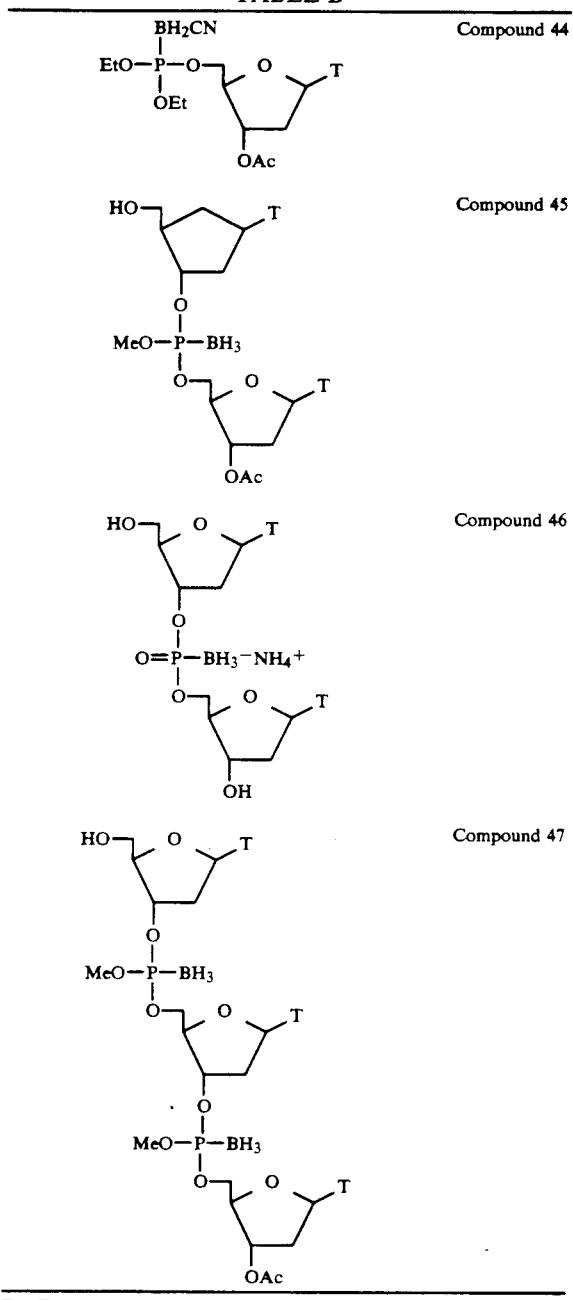

T = Thymidine

Boron analogs of amino acids and related compounds in respect of the present invention have been found particularly useful in lowering blood and urine hydroxyproline levels, in lowering urine calcium excretion, in stabilizing lysosomal hydrolytic enzymatic activities, in inhibiting proteolytic enzymes (e.g., trypsin, collagenase, elastase, etc.), and in inhibiting prostaglandin synthetase activity while elevating cAMP levels.

In addition to anti-osteoporosis activity, many potentially useful organic boron compounds suitably employed in the practice of the present invention have other pharmacological and pharmaceutical activity, including anti-inflammatory, anti-hyperlipidemic, and antineoplastic activity. Accordingly, such compounds also have utility in treating mammals for inflammation, hyperlipidemia, and neoplasia conditions, when such conditions are present in the mammalian subject being treated with such anti-osteoporosis agents.

In this respect, inflammation and the subsequent biochemical and physiological changes associated therewith have been shown to be present in the incidence and development of a number of disease states. Not all facets of the inflammation process are present in each disease state. With an increased understanding of the prostaglandin, thromboxane and leukotriene systems, it known that inflammation plays a role in cystic fibrosis, neonatal hypoxemia, pulmonary hypertension, adult respiratory distress syndrome, psoriasis, spondyloarthritis, rheumatoid arthritis, gout, inflammatory bowel disease, and myocardial infarctions. In consequence, the organic boron compounds employed in the practice of the present invention which exhibit anti-inflammatory activity may be usefully employed to combat such disease states with which inflammation is associated.

A preferred aspect of the present invention comprehends a method of combatting osteoporosis in an animal subject, e.g., mammal, in need of such treatment, by administering to the animal subject an osteoporosis-combatting amount of the organic boron compound.

Subjects to be treated by the disease-combatting method of the present invention include both human and non-human animal (e.g., bird, dog, cat, cow, horse,) subjects, and are preferably mammalian subjects.

Animal subjects are administered the organic boron compounds at a daily dose of preferably at least about 0.1 mg/kg weight of the animal subject, more preferably at least about 0.5 mg/kg, and most preferably at least about 2 mg/kg. The daily dose preferably is not more than about 200 mg/kg, more preferably not more than about 100 mg/kg, and most preferably not more than about 50 mg/kg.

In practicing the method of the present invention, the organic boron compounds may be administered per se or as components of a pharmaceutically acceptable composition. When used in medicine, the form of the organic boron compounds should be both pharmacologically and pharmaceutically acceptable.

Thus, the present invention may be practiced with the boron compounds being provided in pharmaceutical formulations, both for veterinary and for human medical use, comprising the active agent (the organic boron compound) together with one or more pharmaceutically acceptable carriers thereof and optionally any other therapeutic ingredients. The carrier(s) must be pharmacutically acceptable in the sense of being compatible with the other ingredients of the formulation and not unsuitably deleterious to the recipient thereof. The active agent is provided in an amount effective to achieve the desired pharmacological effect, as described above, and in a quantity appropriate to achieve the desired daily dose.

The formulations include those suitable for oral, rectal, topical, nasal, ophthalmic, or parenteral (including subcutaneous, intramuscular, and intravenous) administration. Formulations suitable for parenteral administration are preferred.

The formulations may conveniently be presented in unit dosage form and may be prepared by any of the methods well known in the art of pharmacy. All methods include the step of bringing the active compound into association with a carrier which constitutes one or more accessory ingredients. In general, the formulations may be prepared by uniformly and intimately bringing the active compounds into association with a liquid carrier, a finely divided solid carrier, or both, and then, if necessary, shaping the product into desired formulations.

Formulations of the present invention suitable for oral administration may be presented as discrete units such as capsules, cachets, tablets, or lozenges, each containing a predetermined amount of the active ingredient as a powder or in the form of granules; or as a suspension in an aqueous liquor or a non-aqueous liquid, such as a syrup, an elixir, an emulsion, or a draught.

A tablet may be made by compression or molding, optionally with one or more accessory ingredients. Compressed tablets may be prepared by compressing in a suitable machine, with the active compound being in a free-flowing form such as a powder or granules which optionally is mixed with a binder, disintegrant, lubricant, inert diluent, surface active agent, or discharging agent. Molded tablets comprised of a mixture of the powdered active compound with a suitable carrier may be made by molding in a suitable machine.

A syrup may be made by adding the active compound to a concentrated aqueous solution of a sugar, for example sucrose, to which may also be added any accessory ingredient(s). Such accessory ingredient(s) may include flavorings, suitable preservatives, agents to retard crystallization of the sugar, and agents to increase the solubility of any other ingredient, such as a polyhydroxy alcohol, for example glycerol or sorbitol.

Formulations suitable for parenteral administration conveniently comprise a sterile aqueous preparation of the active compound, which preferably is isotonic with the blood of the recipient (e.g., physiological saline solution).

Nasal spray formulations comprise purified aqueous solutions of the active compound with preservative agents and isotonic agents. Such formulations preferably are adjusted to a pH and isotonic state compatible with the nasal mucous membranes.

Formulations for rectal administration may be presented as a suppository with a suitable carrier such as cocoa butter, hydrogenated fats, or hydrogenated fatty carboxylic acids.

Ophthalmic formulations are prepared by a similar method to the nasal spray, except that the pH and isotonic factors are preferably adjusted to match that of the eye.

Topical formulations comprise the active compound dissolved or suspended in one or more media, such as mineral oil, petroleum, polyhydroxy alcohols, or other bases used for topical pharmaceutical formulations.

In addition to the aforementioned ingredients, the formulations of this invention may further include one or more accessory ingredient(s) selected from diluents, buffers, flavoring agents, binders, disintegrants, surface active agents, thickeners, lubricants, preservatives (including antioxidants), and the like.

The following Examples are provided to illustrate the present invention, and should not be construed as limiting thereof. Compounds are identified in the first instance by a name or a chemical formula, and a reference number, and may thereafter be identified solely by reference number, for ease of reference.

For ease of reference in respect of the following examples, the test procedures for the in vivo and in vitro tests are summarized below:

In Vivo Rodent Screens:
Anti-inflammatory Screen- $Cf_1$- male mice-Winter's Test 2% carrageenan S.C. plantar surface of hind foot, drugs administered @8 or 10 mg/kg I.P. 2X Anti-pyretic Screen-Sprague Dawley male rats 44% Baker's yeast S.C. drugs administered @2.5 or 5 mg/kg/ I.P. rectal temperature taken at 2, 4, and 6 hr.

Writhing reflex- $Cf_1$-male mice- 0.6% acetic acid I.P. drugs administered @20 mg/kg/ I.P. 20 min. later - the # of stretches/10 min.

Hot Plate Tail Flick Test-$Cf_1$-male mice drugs administered @20 mg/kg/ I.P. 5 min later-determined time in seconds to lift tail.

Chronic Adjuvant Arthritis Screen- Sprague Dawley male rats. *Mycobacterium butyricum* in mineral oil S.C. drugs administered @2.5 mg/kg/day for 3 weeks.

Anti-pleursity Screen- Sprague Dawley male rats 0.316% Evans blue +carrageenan in pleural cavity drugs administered at 2.5 mg/kg after 1, and 3 hr.

Ulcerogenic Test- Sprague Dawley male rats drugs administered @2.5 mg/kg/day for 3 weeks gastric and duodenum mucosa examined for lesions.

In Vitro Mode of Action Study
Tissues:
1. $Cf_1$ male mouse hepatic 10% homogenates in 0.25M sucrose+0.001MEDTA, pH 7.2.
2. PMNs-polymorphonuclear neutrophils-rat peritoneal cavity 0.5% oyster glycogen.
3. Mouse macrophages J774A.1 BALB/c
4. Osteoporosis Human Fibroblast-CRL-1140, Be SA1
5. Human peripheral leukocytes, RPMI-1788

Lysosomal Enzymes - free and total [triton X-100].
1. Acid phosphatase -beta glycerol-3-phosphate, pH 5.0, released IP 720 nm.
2. Acid Cathepsin D -azocasein-pH 5.0, hydrolytic azo-peptide produce 366 nm.
3. Aryl sulphatase- p-nitrocatechol sulfate, pH 5. 8 p-nitro-catechol product 510 nm.

Proteolytic Enzymes-
1. Trypsin- N-benzoyl-L-arginine ethyl ester pH 8.0, hydrolytic product 253 nm.
2. Elastase- N-succinyl-L-alanyl-L-alanine-p-nitroanilide, pH 8.0, p-nitro anilide 410 nm.
3. Collagenase I, *Clostridium histolyticum*, bone, skin, tendon, blood vessel, dentine, GI. substrate: rat collagen, N-[propionate-2-3-$^3$H] propionylated measured as dpm released.
4. Collagenase II, *Clostridium histolyticum*, cartilage collagen.

cAMP levels Gilman's radioimmune assay. $^3$H(G)Cyclic-3′, 5′-adenosine monophosphate.

Prostaglandin synthetase purified beef seminal vesicle $^3$H arachidonic acid (86.2 Ci/mmol), tlc separation.

5′-Lipoxygenase-$^3$H-arachidonic acid, calcium ionophore A 23187, tlc-5-hydroxy-eicostetraenoic acid, [5-HETA].

Oxidative phosphorylation- Gilson oxygraph-substrate-Succinate or alpha ketoglutarate measured state 3 and 4, basal and ATP coupled respiration.

Chrmotaxis PMNs migration Nelson's method *E. coli* endotoxin- migration measured in microns.

Protection against free radicals generation-Fenton reaction.

Set out below, in respect of various tests hereinafter referenced, is a listing of literature-based specifications of the methodology therefor:

| Test | Reference |
|---|---|
| percent inhibition anti-inflammation test-Cf$_1$ mouse | Winter, C.A., et al, Proc. Soc. Exp. Biol. Med., 111, 544, 1962; Roszkowski, A. P., et al, J. Pharmacol. Exp. Ther., 179, 114, 1971. |
| porcine pancreatic elastase activity in vitro | Kleinerman, J., et al, Am. Rev. Respiratory. Dis., 121, 381, 1980. |
| Trypsin (BAEE) activity - in vitro | Schleuning, W.D., et al, Methods in Enzymol. XLV, p.330, 1976. |
| Cathepsin azo casein activity - in vitro | Hall, I.H., et al, Jn. Acta Pharm. Nord., 2, 387, 1990. |
| Acid phosphatase activity - in vitro | Hall, I.H., et al, J. Med. Chem. 19, 1257, 1976. |
| Aryl sulfatase activity - in vitro | Roy, A.B., Biochem. J., 53, 12, 1953. |
| Elastase activity - in vitro Uptake of boron analogs of amino acids, peptides and nucleosides in human and Chinese hamster ovary cells grown in tissue culture, and cytotoxicity against growth of human osteosarcoma and human | Kleinerman, J., et al, . Hu, C.L., et al, Anal. Biochem., 88, 683, 1978; Murthy, G., et al Biochem. J., 199, 807, 1981; Cawston, T.E., et al, Anal. Biochem., 99, 340, 1979. |
| osteoporosis fibroblastic cells Urine ketosteroid | Sigma Kit No. 270, Sigma Chemicals Co., St. Louis, Mo. |
| Calcium serum and urine levels | Sigma Kit No. 587, Sigma Chemicals Co., St. Louis, Mo. |
| Hydroxyproline serum and urine levels | Podenphant, J., et al, Clin. Chemica. Acta, 142, 145, 1984. |
| Phosphorus serum and urine levels | Chen, P.S., et al, Anal. Chem., 28, 1756, 1956. |
| Anti-arthritis effect - rats | Waxman, B.H., et al, J. Immunol., 85, 403, 1960. |
| Writhing reflex - mice | Hendershot, L.C., et al, J. Pharm. Expt. Therp., 125, 237, 1959. |
| Tail Flick test - mice | Hall, I.H., et al, J. Pharm. Sci., 69, 1451, 1980. |
| Anti-pleurisy effect - rats | Sancilo, L.F., Pros. Soc. Expt. Biol. and Med., 127, 597, 1968. |
| Fenton reaction | Kurchandy, E., et al, Intl. J. of Pharmaceutic., 57, 173, 1989. |
| Prostaglandin synthesis | Glatt, N., et al, Agents and Actions, 7, 321, 1977; Tomlinson R.V., et al, Biochem. Biophys. Res. Comm., 46, 352, 1972. |
| 5′-lipoxygenase | Mylari, B.L., et al, J. Med. Chem., 33, 2019, 1990. |

EXAMPLE I

In this test, in vivo anti-inflammatory activity in rodents was evaluated for the compounds and with the results set out in Table I below.

TABLE 1

In Vivo Anti-inflammatory Activity in Rodents

| (N=6) Compound | LD$_{50}$ mg/kg | Anti-inflammatory | Writhing | Anti-arthritic | Anti-pleurisy |
|---|---|---|---|---|---|
| 1. O(CH$_2$CH$_2$)$_2$)NHBH$_3$ | 475 | 55 | 15 | 33 | — |
| 2. (CH$_3$)$_3$N.BH$_2$CN | 70 | 42 | 18 | 4 | 65 |
| 3. (CH$_3$)$_3$N.BH$_2$COOH | 1800 | 79 | 29 | 53 | — |
| 4. [Na(H$_3$N.BH$_2$(CN)$_6$]I | 100 | 57 | 12 | 0 | 51 |
| 5. [CH$_2$N(CH$_3$)$_2$BH$_2$COOH]$_2$ | 1000 | 58 | 55 | 24 | — |
| 6. (CH$_3$)$_3$NBH$_2$COOCH$_2$CH$_3$ | 140 | 74 | 89 | 13 | 61 |
| 7. Indomethacin 10 mg/kg | 28 | 22 | 43 | 27 | — |

The compounds tested did not lower induced elevated body temperature of rats. There was evidence that gastrointestinal lesions were produced by the agents in rats. There was no effect on chemotaxis.

EXAMPLE II

In this example, biochemical effects of the organic boron compounds of Example I were evaluated for mouse liver and PMNs lysosomal enzyme activities, with the results shown in Table II below.

TABLE II

| (N = 6) 5 × 10$^{-6}$M Compound | Mouse Liver | | Rat PMNs | | PMNs |
|---|---|---|---|---|---|
| | Acid Phosph. | Cathep. | Acid Phoph. | Cathep. | cAMP |
| 1 | 75 + 8 | 107 + 6 | 79 + 5 | 93 + 7 | 107 |
| 2 | 69 + 4 | 6 + 2 | 35 + 5 | 4 + 2 | 245 |
| 3 | 82 + 5 | 56 + 6 | 50 + 3 | 14 + 4 | 99 |
| 4 | 65 + 3 | 3 + 1 | 34 + 6 | 3 + 3 | 361 |
| 5 | 69 + 5 | 23 + 6 | 84 + 4 | 52 + 4 | 155 |
| 6 | | | | 16 + 3 | |
| Indomethacin | 86 + 4 | 67 + 6 | 100 + 2 | 100 + 1 | 80 |
| | 0.753 ug Pi/ hr/mg wet tissue | 7.17 ug pro./ hr/mg wet tissue | 0.26 mg Pi/ hr/10$^{-7}$ cells | 0.225 mg/ hr/10$^{-7}$ cells | 748 p.M/ 10$^{-7}$ |

TABLE II-continued

| (N = 6) 5 × 10$^{-6}$M Compound | % Control | | | | |
|---|---|---|---|---|---|
| | Mouse Liver | | Rat PMNs | | PMNs |
| | Acid Phosph. | Cathep. | Acid Phoph. | Cathep. | cAMP cells |

EXAMPLE III

In this example, prostaglandin synthetase activity and hepatic oxidative phosphorylation were evaluated for the compounds of Exampe I, with the results shown in Table III below.

TABLE III

| 10$^{-6}$M Compound | % Control | | | | |
|---|---|---|---|---|---|
| | Prostaglandin synthetase | Hepatic Oxidative Succinate | | Phosphorylation alpha-Ketoglutrate | |
| | | State 4 | State 3 | State 4 | State 3 |
| 1 | 100 + 5 | 115 + 5 | 66 + 10 | 97 + 29 | 50 + 11 |
| 2 | 59 + 6 | 133 + 20 | 51 + 20 | 85 + 21 | 41 + 9 |
| 3 | 93 + 3 | 122 + 14 | 63 + 4 | 127 + 22 | 70 + 20 |
| 4 | 42 + 5 | 110 + 5 | 31 + 10 | 101 + 25 | 37 + 10 |
| 5 | 60 + 6 | 80 + 11 | 57 + 16 | 122 + 15 | 48 + 30 |
| 6 | — | 119 + 18 | 61 + 19 | 126 + 51 | 54 + 8 |
| Indomethacin [10$^{-4}$M] | 64 + 2 | | | | |
| Control | 100 + 4 6564 DPM/ hr/mg | 100 + 6 9.19 ul/ hr/mg | 100 + 4 13.66 ul/ hr/mg | 100 + 8 3.38 ul hr/mg | 100 + 9 4.93 ul/ hr/mg |

In this test, in vivo activity was determined for rodents With respect to anti-inflammatory activity and writhing reflex. The results are shown in Table IV below.

TABLE IV

| | In Vivo Activity 8 mg/kg I.P. | | |
|---|---|---|---|
| | % Control | | |
| | Anti-Inflammatory Activity | | Writhing Reflex Cf$_1$ Mice |
| Compounds | Mice | Sprague Dawley Rats | |
| 1'. (CH$_3$)$_3$CNH$_2$BH$_3$ | 41 | — | 18 |
| 2'. CH$_3$NH$_2$BH$_2$COOH | 54 | — | 31 |
| 3'. (CH$_3$)$_2$NHBH$_2$COOH | 65 | 55 | 2.0 |
| 4'. (CH$_3$)$_3$NBH$_2$COOH | 58 | 59 | 11.5 |
| 5'. (CH$_3$)$_3$NBH$_2$COOCH$_3$ | 58 | | 2.0 |
| 6'. C$_{18}$H$_{37}$N(CH$_3$)$_2$BH$_2$COOH | 80 | | 14.1 |
| 7'. C$_{16}$H$_{33}$N(CH$_3$)$_2$BH$_2$COOH | 58 | | 54.0 |
| 8'. (C$_6$H$_5$)$_3$PBH$_2$COOH | 40 | | 18.7 |
| 9'. (CH$_3$)$_2$NHBH$_2$C(O)NHC$_2$H$_5$ | 59 | 41 | 26.9 |
| 10'. (CH$_3$)$_2$NHBH$_2$CN | 49 | 61 | 14.7 |
| 11'. (CH$_3$)$_3$NBH$_2$CN | 42 | 65 | 18.0 |
| 12'. O(CH$_2$CH$_2$)$_2$NHBH$_3$ | 55 | | 15.2 |
| 13'. Na$_2$BH$_3$COO | 42 | 55 | 17.4 |
| 14'. (CH$_3$)$_3$NBH$_2$C(O)NHOH. HB(C$_6$H$_5$)$_4$ | 56 | 60 | 50.0 |
| 15'. C$_5$H$_5$NBH$_2$COOH | 51 | | 50 |
| 16'. (CH$_3$)$_3$NB(CN)$_2$CH$_3$ | 59 | | 33.9 |

EXAMPLE V

In this test, the effects of selected boron compounds of Example IV were evaluated for mouse hepatic lysosomal enzyme activities, for acid phosphatase, cathepsin D, and aryl sulphatase, the results are shown in Table 5 below.

TABLE V

The Effects of Boron Derivatives on Mouse Hepatic Lysosomal Enzyme Activities 60 min Incubation IC$_{50}$ values 10$^{-6}$M.

| Compound # | Acid Phosphatase | Cathepsin D | Aryl Sulphatase |
|---|---|---|---|
| 1' | 7.7 | 5.8 | |
| 3' | 7.89 | 3.76 | |
| 5' | 7.37 | 6.59 | |
| 6' | 9.67 | 6.21 | |
| 7' | 8.86 | 2.82 | |
| 10' | 8.90 | 3.20 | |
| 11' | 3.51 | 0.72 | |
| 12' | 8.95 | 0.88 | |
| 14' | 4.22 | 3.66 | 5.85 |
| 15' | 10.02 | 4.80 | |

EXAMPLE VI

Selected boron compounds from Example IV were evaluated for their effects on mouse hepatic proteolytic enzyme activity and 5'-lypoxygenase activity. The results are shown in Table VI below.

TABLE VI

The Effects of Boron Derivatives on Mouse Hepatic Proteolytic Enzymes and 5'-Lipoxygenase Activities 60 min Incubation IC$_{50}$ values 10$^{-6}$M.

| Compound # | Trypsin | Elastase | 5'-lipoxygenase |
|---|---|---|---|
| 2' | | | 64.6 |
| 3' | 0.83 | 25.9 | |
| 5' | 1.19 | 37.4 | 66.6 |
| 6' | 0.23 | 22.9 | |
| 7' | 1.16 | 49.6 | 55.8 |
| 9' | | | 43.5 |
| 10' | | | 22.9 |
| 12' | 0.51 | 4.4 | 66.9 |

EXAMPLE VII

The effects of selected boron compounds of Example IV were tested for their effects on mouse macrophage cultured cells, with respect to activity of cathepsin D, acid phosphatase, and aryl sulphatase. The results are shown in Table VII below.

TABLE VII

The Effects of Boron Derivatives on Mouse Macrophage Cultured Cells Grown in DMEM +10% FCS +P/S, $10^{-6}$ cells

| 60 min Incubation Compound # | IC$_{50}$ values $10^{-6}$M. | | |
|---|---|---|---|
| | Cathepsin D | Acid Phosphatase | Aryl Sulphatase |
| 1' | 8.08 | — | 4.62 |
| 2' | 9.45 | 0.90 | 8.30 |
| 3' | 6.39 | 4.75 | — |
| 4' | 6.71 | 1.04 | 7.42 |
| 5' | 8.29 | 3.55 | — |
| 6' | 5.10 | 5.34 | — |
| 7' | 7.18 | 0.94 | 9.71 |
| 8' | 5.52 | 1.08 | 8.58 |
| 9' | 3.95 | 1.12 | 9.27 |
| 10' | 5.54 | 1.13 | 9.00 |
| 11' | 6.34 | 1.05 | 9.29 |
| 12' | 0.76 | 3.18 | — |
| 13' | 4.57 | 0.82 | 5.43 |
| 14' | 1.69 | 3.96 | 1.37 |
| 16' | 6.89 | 1.10 | 8.48 |

EXAMPLE VIII

The effects of selected boron compounds of Example IV were evaluated on proteolytic enzyme activity and prostaglandin cyclooxygenase activity of mouse macrophages. Results are set out in Table VIII below.

TABLE VIII

The Effects of Boron Derivatives on Proteolytic Enzyme Activities and Prostaglandin Cyclooxygenase Activity of Mouse Macrophages 60 min. Incubation IC$_{50}$ values × $10^{-6}$M.

| Compound # | Trypsin BAEE | Elastase | Prostaglandin Cyclooxygenase |
|---|---|---|---|
| 1' | 2.09 | 0.22 | 4.19 |
| 2' | 2.34 | 2.32 | 3.50 |
| 3' | 3.10 | 2.67 | 2.91 |
| 4' | 2.78 | 2.14 | 2.81 |
| 5' | 3.23 | 8.76 | 2.41 |
| 6' | 2.07 | 6.29 | 2.51 |
| 7' | 1.26 | 1.80 | 2.55 |
| 8' | 1.77 | 3.04 | 3.53 |
| 9' | 2.03 | 3.29 | 5.19 |
| 10' | 2.44 | 2.53 | 5.92 |
| 11' | 1.41 | 1.35 | 5.88 |
| 12' | 2.39 | 5.94 | 1.47 |
| 13' | 2.25 | 3.07 | 6.79 |
| 14' | 2.14 | 1.49 | 1.61 |
| 16' | 1.62 | 2.02 | 3.05 |

3H-Arachidonic acid conversion to Pg-E$_2$ was reduced 43% in CF$_1$ hepatic liver, and 29% in macrophage by compound 7'. Compounds 7' and 8' reduced hepatic Pg-E$_2$ synthesis by 32% and macrophage Pg-E$_2$ synthesis by 20%. When osteoporosis fibroblasts (obtained from American Tissue Culture) were examined, Compounds 7'. and 8'. were found to be potent inhibitors of lysosomal and proteolytic enzymes of these cells, as shown by the results in Table XXIII.

TABLE VIIIA

| | Osteoporosis Fibroblasts Enzyme Activity In Vitro | | | | |
|---|---|---|---|---|---|
| Com-pd. # | IC$_{-50}$ × $10^{-6}$M | | | | |
| | Trypsin (BAEE) | Cathepsin Azo-casein | Acid Phosphatase | Aryl Sulfatase | Elastase |
| 7' | 7.4 | 2.06 | 16.6 | 9.01 | 3.86 |
| 8' | 5.7 | 6.42 | 15.3 | 9.33 | 1.96 |

EXAMPLE IX

Selected compounds of Example IV were tested to determine their effects on commercial enzyme preparations, including *Clostridium histolyticum* type I and II collagenases, porcine pancreatic elastase, and beef prostaglandin cyclooxygenase. Results are set out in Table IX below.

TABLE IX

Effects of Boron Derivatives on Commercial Enzyme Preparations

| | IC$_{50}$ values × $10^{-6}$M. | | | |
|---|---|---|---|---|
| | Clostridium histolyticum Collagenase | | Porcine | Beef |
| Compound | Type I | Type II | Pancreatic Elastase | Prostaglandin Cyclooxygenase |
| 2' | | 101 | | |
| 3' | 667 | | 37.3 | 3.25 |
| 5' | 797 | 124 | 32.8 | 2.98 |
| 6' | 663 | | 27.6 | 1.92 |
| 7' | 615 | 109 | 49.7 | 2.86 |
| 8' | | 107 | | |
| 10' | | 106 | | |
| 11' | | 113 | | 5.9 |
| 12' | 783 | 896 | 14.9 | 2.36 |
| 14' | | | | 1.30 |
| 15' | | | | 7.60 |
| 16' | | 110 | | |

EXAMPLE X

Selected boron compounds of Example IV were tested to determine their effects on human osteoporosis fibroblasts tissue culture, with respect to cathepsin D, acid phosphatase, and aryl sulphatase. Results are shown in Table X below.

TABLE X

The Effects of Boron Derivatives on Human Osteoporosis Fibroblasts Tissue Culture Grown in DMEM +10% FCS + P/S

| Compound # | IC$_{50}$ values × $10^{-6}$M. | | |
|---|---|---|---|
| | Cathepsin D | Acid Phosphatase | Aryl Sulphatase |
| 1' | 6.42 | 10.2 | 9.14 |
| 4' | 1.10 | 17.6 | 8.59 |
| 7' | 2.06 | 16.6 | 9.01 |
| 8' | 6.42 | 15.3 | 9.33 |
| 9' | 1.93 | 8.6 | 7.63 |
| 10' | 1.28 | 8.7 | 7.91 |
| 11' | 2.01 | 15.9 | 8.87 |
| 12' | 4.40 | 10.3 | 8.99 |
| 13' | 1.19 | 6.5 | 8.19 |
| 15' | 8.16 | 18.3 | 8.16 |

EXAMPLE XI

In this example, certain boron compounds of Example IV were evaluated to determine their effect on proteolytic enzymes and prostaglandin cycloygenase activities of human osteoporosis fibroblasts. The activity values are set out in Table XI below.

TABLE XI

The Effects of Boron Derivatives on Proteolytic Enzymes and Prostaglandin Cyloxygenase Activities of Human Osteoporosis Fibroblasts 60 min Incubation IC$_{50}$ values × $10^{-6}$M.

| Compounds # | Trypsin BAEE | Elastase | Prostaglandin Cyclooxygense |
|---|---|---|---|
| 1' | 7.00 | 3.15 | 3.94 |
| 4' | 6.14 | 1.31 | 4.24 |
| 7' | 7.40 | 3.86 | 6.77 |
| 8' | 5.70 | 1.96 | 5.49 |
| 9' | 4.36 | 0.98 | 8.05 |
| 10' | 6.43 | 3.36 | 5.58 |
| 11' | 3.98 | 3.29 | 4.26 |
| 12' | 7.88 | 1.84 | 3.41 |

TABLE XI-continued

The Effects of Boron Derivatives on Proteolytic Enzymes and Prostaglandin Cycloxygenase Activities of Human Osteoporosis Fibroblasts 60 min Incubation IC$_{50}$ values $\times$ 10$^{-6}$M.

| Compounds # | Trypsin BAEE | Elastase | Prostaglandin Cyclooxygense |
|---|---|---|---|
| 13' | 7.51 | 3.01 | 5.51 |
| 16' | 3.35 | 3.60 | 9.29 |

EXAMPLE XII

In this test, selected compounds of Example IV were tested to determine their effects on human leukocyte tissue culture cells, with respect to 5'lypoxygenase and cathepsin. Results are shown in Table XII below.

TABLE XII

The Effects of Boron Derivatives on Human Leukocytes Tissue Culture Cells Grown in RMPI 1640 + 15% FCS + P/S 60 min Incubation IC$_{50}$ values $\times$ 10$^{-5}$M.

| Compound # | 5'Lipoxygenase | Cathepsin |
|---|---|---|
| 2' | 5.83 | 7.03 |
| 5' | 5.37 | 5.97 |
| 7' |  | 6.46 |
| 8' | 4.77 | 7.25 |
| 10' |  | 5.38 |
| 11' | 6.42 | 7.71 |
| 12' |  | 7.28 |
| 16' | 3.28 | 6.52 |

EXAMPLE XIII

In this example, the boron compounds identified in Table XIII below were tested for in vivo effects on serum and urine levels of hydroxyproline, calcium and inorganic phosphorous of Cf$_1$ male mice, at the dosage stated in the table, with the results set forth therein.

TABLE XIII

The In Vivo Effects of Boron Derivatives on Serum and Urine Levels of Hydroxyproline, Calcium and Inorganic Phosphorous of Cf$_1$ Male Mice Dosed at 8 mg/kg/day I.P. 14 Days

| (N=6) Compounds | % Control | | | | | |
|---|---|---|---|---|---|---|
|  | Hydroxyproline | | Calcium | | Phosphorus | |
|  | serum | urine | serum | urine | serum | urine |
| (CH$_3$)$_2$N(C$_{16}$H$_{33}$)BH$_2$COOH | 84.1 | 28.7 | — | 80.7 | — | — |
| Ph$_3$PBH$_2$COOH | 60.5 | 30.0 | — | 83.5 | — | — |
| (CH$_3$)$_2$N(C$_{18}$H$_{37}$)BH$_2$COOH | 76.4 | 60.6 | 135.4 | 64.4 | 86.2 | 65.4 |
| CH$_3$NH$_2$BH$_2$COOH | 71.7 | 42.5 | 109.7 | 50.8 | 81.6 | 39.6 |
| CH$_3$NH$_2$BH$_2$COOCH$_3$ | 68.0 | 144.1 | 105.1 | 176.9 | 65.3 | 136.8 |
| (CH$_3$)$_3$NBH$_2$COOCH$_3$ | 79.4 | 51.4 | 110.7 | 52.6 | 81.6 | 54.4 |
| CH$_3$CH$_2$NH$_2$BH$_2$COOH | 89.1 | 69.2 | 121.0 | 61.2 | 64.3 | 78.0 |
| (CH$_3$)$_2$NHBH$_2$COOCH$_3$ | 84.4 | 50.5 | 125.4 | 80.7 | 42.8 | 67.8 |

EXAMPLE XIV

In this example, the metal complexes of boron compounds are identified as compounds 21-28 below.

| Reference No. | Complex |
|---|---|
| 21. | Na$_2$BH$_3$COO |
| 22. | Na(CH$_3$)$_3$NBH$_2$COO.(0.25CH$_3$OH) |
| 23. | Na(CH$_3$)$_2$NHBH$_2$COO.(0.45H$_2$O) |
| 24. | [Fe$_3$O((CH$_3$)$_3$NBH$_2$COO)$_6$(CH$_3$OH)$_3$]NO$_3$.CH$_3$CN |
| 25. | [Fe$_3$O((CH$_3$)$_3$NBH$_2$COO)$_6$(H$_2$O)$_3$]Cl |
| 26. | [Cr$_3$O((CH$_3$)$_3$NBH$_2$COO)$_6$(H$_2$O)]NO$_3$.CH$_3$OH.CH$_3$CN |
| 27. | Cis-[Co(en)$_2$((CH$_3$)$_3$NBH$_2$COO)$_2$]Cl.2.5H$_2$O.(0.5CH$_3$OH) |
| 28. | Ca((CH$_3$)$_3$NBH$_2$COO)NO$_3$.CH$_3$COCH$_3$.(0.5H$_2$O) | were tested to determine their in vivo anti-inflammatory effects in the test, and with the results, identified in Table XIV below.

TABLE XIV

| Compound # | Anti-Inflammation Cf$_1$ Mice | Anti-Arthritis Rats | Writhing Reflex Mice | Tail Flick Mice | Anti-Pleurisy Rats |
|---|---|---|---|---|---|
| 21 | 41.7 | 55.2 | — |  |  |
| 22 | 73.4 |  | 76.5 | 101 |  |
| 23 | 68.5 |  | 70.4 | 156 |  |
| 24 | 81.6 |  | 42.9 | 338 |  |
| 25 | 74.2 |  | 36.4 | 599 |  |
| 26 | 58.5 | 78.0 | 85.4 | 184 | 40.0 |
| 27 | 49.6 | 70.0 | 66.2 | 150 | 96.3 |
| 28 | 65.0 |  | 66.4 | 169 | 50.1 |

EXAMPLE XV

The compounds of Example XIV (metal complexes of boron derivatives, Nos. 21-28) were evaluated for their effect on mouse hepatic lysosomal enzyme activities, for cathepsin D, acid phosphatase, and aryl sulphatase. Results are shown in Table XV below.

TABLE XV

The Effects of Metal Complexes of Boron Derivatives on Mouse Hepatic Lysosomal Enzyme Activities

| 60 min Incubation Compound # | IC$_{50}$ values $\times$ 10$^{-6}$ M | | |
|---|---|---|---|
|  | Cathepsin D | Acid Phosphatase | Aryl Sulphatase |
| 21 | 6.19 | 4.00 | 4.34 |
| 22 | 6.69 | 3.56 | 5.15 |
| 23 | 7.65 | 3.58 | 2.83 |
| 24 | 6.84 | 5.60 | 2.57 |
| 25 | 8.17 | 4.14 | 2.33 |
| 26 | 5.47 | 6.99 | 7.73 |
| 27 | 7.80 | 4.25 | 5.89 |
| 28 | 4.58 | 7.66 | 3.05 |

EXAMPLE XVI

The metal complexes of boron derivatives of Example XIV were evaluated for their effects on proteolytic enzymes and prostaglandin cyclooxygenase activity. Results are set out in Table XVI below.

TABLE XVI

The Effects of Metal Complexes of Boron Derivatives on Proteolytic Enzyme and Prostaglandin Cyclooxygenase Activity 60 min Incubation IC$_{50}$ values $\times$ 10$^{-6}$ M.

| Compound # | Mouse Hepatic Trypsin | Porcine Seminal Vesicles Pg. cyclooxygenase | Commercial Collagenase |
|---|---|---|---|
| 21 |  |  |  |
| 22 | 9.98 | 2.40 | 490 |
| 23 | 9.95 | 3.10 | 506 |

TABLE XVI-continued

The Effects of Metal Complexes of Boron Derivatives on Proteolytic Enzyme and Prostaglandin Cyclooxygenase Activity 60 min Incubation IC$_{50}$ values × 10$^{-6}$ M.

| Compound # | Mouse Hepatic Trypsin | Porcine Seminal Vesicles Pg. cyclooxygenase | Commercial Collagenase |
|---|---|---|---|
| 24 | 9.93 | 2.90 | 478 |
| 25 | 9.91 | 4.17 | 475 |
| 26 | 9.96 | 2.14 | 567 |
| 27 | 9.88 | 4.01 | 522 |
| 28 | 9.99 | 2.57 | 495 |

EXAMPLE XVII

The metal complexes of boron derivatives of Example XIV were tested for their effects on mouse macrophage lysosomal enzyme activities, for cathepsin D, acid phosphatase, and aryl sulphatase. Results are set out in Table XVII below.

TABLE XVII

The Effects of Metal Complexes of Boron Derivatives on Mouse Macrophage Lysosomal Enzyme Activities 60 min Incubation
IC$_{50}$ values × 10$^{-6}$ M.

| Compound # | Cathepsin D pH 5.0 | Acid Phosphatase | Aryl Sulphatase |
|---|---|---|---|
| 21 | 4.57 | 0.82 | 5.43 |
| 22 | 1.92 | 2.00 | 1.33 |
| 23 | 2.28 | 1.42 | 1.60 |
| 24 | 2.85 | 2.09 | 1.95 |
| 25 | 3.39 | 2.44 | 2.75 |
| 26 | 2.49 | 2.48 | 1.20 |
| 27 | 3.83 | 2.92 | 1.95 |
| 28 | 2.38 | 3.08 | 2.38 |

EXAMPLE XVIII

The metal complexes of Example XIV were tested to determine their effects on mouse macrophage proteolytic enzyme and prostaglandin cyclooxygenase activities, yielding the results in Table XVIII below.

TABLE XVIII

The Effects of Metal Complexes of Boron Derivatives on Mouse Macrophage Proteolytic Enzyme and Prostaglandin Cyclooxygenase Activities 60 min Incubation
IC$_{50}$ values × 10$^{-6}$ M.

| Compound # | Trypsin BAEE | Elastase | Prostaglandin Cyclooxygenase |
|---|---|---|---|
| 21 | 2.25 | 3.07 | 15.59 |
| 22 | 2.27 | 7.26 | 2.41 |
| 23 | 2.21 | 6.35 | 2.07 |
| 24 | 2.37 | 3.92 | 2.34 |
| 25 | 1.81 | 4.11 | 2.08 |
| 26 | 2.10 | 5.09 | 1.62 |
| 27 | 1.38 | 9.77 | 2.09 |
| 28 | 2.38 | 5.93 | 1.92 |

EXAMPLE XIX

In this example, deoxynucleoside boron derivatives of the structure specified in Tables A and B hereinabove as compound Nos. 29–47 were tested to determine their effects on inflammation processes. Results are shown in Table XIX below.

TABLE XIX

The Effects of Deoxynucleoside Boron Derivatives on Inflammation Processes

| Anti-inflammatory Activity 8 mg/kg | | Mouse Hepatic Cathepsin D | Human Leukocyte | Leukocyte 5' lipoxygenase |
|---|---|---|---|---|
| Compound # | % Control | | IC$_{50}$ values × 10$^{-6}$M. | |
| 29 | 49.2 | 79.6 | 31.8 | 8.85 |
| 30 | 75.3 | | | |
| 31 | 70.9 | | | |
| 32 | 55.4 | | | |
| 33 | 78.4 | | | |
| 34 | 76.5 | | | |
| 35 | 57.5 | 58.1 | 33.4 | 10.1 |
| 36 | 70.6 | | | |
| 37 | 63.1 | | | |
| 38 | 48.2 | 59.7 | 13.9 | 7.72 |
| 39 | 48.3 | 26.0 | 8.72 | 12.8 |
| 40 | 55.2 | 27.2 | 6.12 | 3.88 |
| 41 | 87.8 | | | |
| 42 | 63.0 | 30.6 | 7.31 | 6.64 |
| 43 | 66.0 | | | |
| 44 | 66.8 | | | |
| 45 | 73.9 | | | |
| 46 | 63.1 | | | |
| 47 | 60.0 | | | |

EXAMPLE XX

Boron analogs of amino acids, peptides and nucleosides are readily taken up in human and chinese hamster ovary cells grown in tissue culture. The cytotoxic effect of Compounds 7', 8', and 5', (identified in Example XX) against the growth of (ATCC) human osteosarcoma and human osteoporosis fibroblastic cells (as shown by the results in Table XXIV), evidences that these compounds are entering the cells. A boron-containing nucleoside analog was found in the bone at 1% of the administered does in an in vivo experiment with mice. Thus, boron analogs of endogenous intermediate metabolites enter various tissue types, including bone.

TABLE XX

| Compound # | Cytoxicity | |
|---|---|---|
| | ED-50 μg/ml Osteosarcoma | Osteoporosis Fibroblasts |
| 7'. | 2.47 | 7.39 |
| 8'. | 2.65 | 5.3 |
| 5'. | 5.13 | 7.09 |
| 14'. | 1.14 | 1.21 |

EXAMPLE XXI

Trimethylamine-carboxymethoxyborane, tetrakis-μ(trimethylamine-boranecarboxylato-bis(trimethylamine-carboxyborane-dicopper(II) and N,N-dimethyl-n-octadecylamineborane were evaluated for acute toxicity.

CF$_1$ male mice (~28–30 gm) were treated at 1, 2 or 5×the anti-inflammatory theapeutic dose i.p for 7 days. The mice were sacrificed by cervical dislocation. Food consumption (Ralston Purina Co.) was monitored daily and water was ad libitum. The mice were maintained on a 12 h cycle of light and dark daily at 22° C.

At the time of the sacrifice, the major organs were excised, trimmed of fat, weighed and expressed as 100 g of body weight. Blood was obtained from the carotid and centrifuged at 3500 g×10 min to obtain the serum. Chemical or enzymatic assays were performed with Sigma Chemical Kits; urea nitrogen (BUN, No. 640), alanine amino transferase (SGPT, No. 505), alkaline phosphatase (AP, No. 104), glucose (No. 510), lactic dehydrogenase (LDH, No. 500), creatine phosphokinase (CP-kinase, No. 661), and total and direct bilirubin (No. 605), Serum triglycerides were determined with a diagnostic kit from Boehringer Mannheim; serum cholesterol was determined by the method of Ness et al (Clin. Chem. Acta 10, 229 (1964). Albumin and total protein were determined according to Lowery et al (J. Biol. Chem. 193, 265 (1951). Cholic acid and uric acid were determined as outlined by Tietz (Fundamentals of Clinical Chemistry, p. 249–1057, Saunders, Philadelphia Pa. 1976).

Amine borane compounds (0 to 100 mg/kg) were administered to $CF_1$ male mice as a single injection with six mice for each dosage. Mice were weighed daily and the number of deaths was recorded each day for a 14 day period. The $LD_{50}$ value was determined by the procedure of S.C. Gad and C.S. Weil, "Statistics for Toxicologists" in Principles and Methods of Toxicology, A.W. Hayes, Ed., 2nd Edition, P 435–483 Raven Press, New York 1982.

Blood was obtained from the caroid; a drop was placed on glass slides and fixed in Wright's stain. Differential white blood cell counts, platelet counts and hematocrit were obtained for each mouse group sacrificed at the specified times.

The animals were killed by carbon dioxide asphyxiation. After all vital signs had ceased, a midline incision was made from the lower jaw to the inguinal area. Spleen, liver, and kidney were excised and weighed, and representative tissue samples were fixed in 10% buffered formalin, trimmed and sectioned at 6 μ in thickness and stained with hematoxylin and eosin.

The results of these tests, to be published in Arch. Pharm. (Weinhiem) 324, (1991), I. Hall, et al, hereby incorporated herein by reference, showed trimethylamine-carbomethoxyborane to be free of toxicity based on mouse organ weights, hematological parameters, clinical chemistry values, and major tissue morphology. The only deleterious effect noted was the slight reduction of hematocrit at 5×the therapeutic dose.

All three drugs in 7 days afforded reductions of serum glucose, cholesterol, and triglyceride levels; however, these were not low enough magnitudes of reduction to be life-threatening in any way. All of the animals survived all of the doses with no observable differences in motor or CNS activities. The clinical chemistry and morphological effects observed appeared to be of the type that would be manageable in a clinical situation since they were not sever in nature.

While the invention has been described herein with reference to illustrative compounds and specific embodiments of the invention, it will be appreciated that numerous variations, modifications, and other embodiments are possible, and accordingly, all such variations, modifications, and embodiments are to be regarded as being within the spirit and scope of the invention.

What is claimed is:

1. A method of combatting osteoporosis in an animal subject, comprising administering to the animal subject an amount of an organic boron compound which (i) is effective against osteoporosis, and (ii) does not cause a statistically significant increase in hydroxylated steroids selected from the group consisting of 17-β-estradiol and testosterone, wherein said organic boron compound is selected from the group consisting of:

(1) organic boron compounds of the formula:

$R_1R_2R_3XBR_4R_5R_6$ wherein:

X is N or P;

$R_1$, $R_2$, $R_3$ are independently selected from H, $C_1$–$C_{20}$ linear or branched alkyl, alkoxy, alkylaryl, aryl, and substituted aryl, or $R_1$, $R_2$, and $R_3$ together with X form a heterocyclic ring structure, with the proviso that when X=N, $R_1$, $R_2$ and $R_3$ are not alkoxy:

$R_4$ and $R_5$ are independently selected from H, $C_1$–$C_{20}$ linear or branched alkyl, aryl, alkylaryl, and substituted aryl: $R_6$ is H, $C_1$–$C_{20}$ linear or branched alkyl, aryl, alkylaryl, substituted aryl, CN, COOH, COOM, $COOR_7$, $CONHR_7$, CONHOH, or COAA, or $R_4$, $R_5$, and $R_6$ together with B form a heterocyclic ring structure:

where:

M is Li, Na, K, or ammonium ion;

$R_7$ is H, $C_1$–$C_{10}$ alkyl, substituted alkyl, aryl, or substituted aryl; and AA is $NHCH(R_8)COOR_9$ or $NHCH(R_8)CONHR_9$ where $R_8$ is selected from the side chains of common amino acids and $R_9$ is H, or $C_1$–$C_5$ alkyl.

(2) organic boron compounds of the formula:

$R_1R_2R_3XBR_4(R_5)_2$ wherein: $R_1$, $R_2$, $R_3$, $R_4$ and X are same as above, and $R_5$ is CN.

(3) organic boron compounds of the formula:

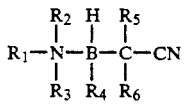

wherein:

$R_1$, $R_2$ and $R_3$ are same as in (1):

$R_4$ is H, $C_1$–$C_{10}$ linear or branched alkyl, alkylaryl, or aryl; and $R_5$ and $R_6$ are independently selected from H, $C_1$–$C_{10}$ alkyl, alkylaryl, aryl, or substuted aryl;

(4) organic boron compounds of the formula:

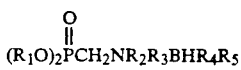

wherein:

$R_1$ is $C_1$–$C_{10}$ linear or branched alkyl, alkylaryl, or aryl;

$R_2$, $R_3$ are independently selected from H, and $C_1$–$C_{10}$ linear or branched alkyl;

$R_4$ is H, $C_1$–$C_{10}$ linear or branched alkyl, alkylaryl, or aryl;

$R_5$ is CN, COOH, $CONHR_6$, or $COOR_6$, wherein $R_6$ is same as $R_7$ in (1);

(5) organic boron compounds of the formula;

wherein;

X is O or S;

$R_1$, $R_2$, $R_3$ are independently selected from H, $C_1$-$C_{10}$ alkyl, alkylaryl, and aryl;

$R_4$ is $NMe_2$ or $R_5$, wherein $R_5$ is $C_1$-$C_{10}$ linear or branched alkyl, alkylaryl, aryl, or substituted aryl;

(6) organic boron compounds of the formula:

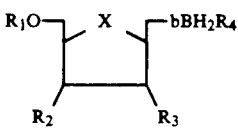

wherein:
X is C or O;
$R_1$ is H or a suitable protecting group;
$R_2$ is H or OH;
$R_3$ is H or OH;
b represents a nucleoside base;
$R_4$ is CN, COOH, $COOR_5$, or $CONHR_5$, wherein $R_5$ is H, $C_1$-$C_{10}$ alkyl, alkylaryl, aryl, or substituted aryl;

(7) organic boron compounds of the formula:

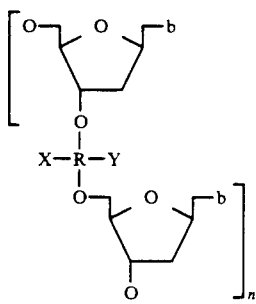

wherein:
n = 1-50;
b is a nucleoside base;
X is O, or OR, wherein R is $CH_3$, $CH_2CH_2CN$, or $CH_2CH_3$; and
Y is $BH_3$, $BH_2CN$, $BH_2COOH$, $BH_2COOR_1$, or $BH_2CONHR$,
wherein $R_1$ is H, or $C_1$-$C_5$ alkyl; and (8) metal complexes of amine-cyanoboranes, and metal complexes of aminecarboxyboranes.

2. A method according to claim 1, wherein the organic boron compound comprises a Lewis base-boron adduct.

3. A method according to claim 1, wherein the organic boron compound is selected from the group consisting of organic boron compounds of the formula:

$R_1R_2R_3XBR_4R_5R_6$ wherein:

X is N or P;
$R_1$, $R_2$, $R_3$ are independently selected from H, $C_1$-$C_{20}$ linear or branched alkyl, alkoxy, alkylaryl, aryl, and substituted aryl, or $R_1$, $R_2$, and $R_3$ together with X form a heterocyclic ring structure, with the proviso that when X=N, $R_1$, $R_2$ and $R_3$ are not alkoxy;

$R_4$ and $R_5$ are independently selected from H, $C_1$-$C_{20}$ linear or branched alkyl, aryl, alkylaryl, and substituted aryl;

$R_6$ is H, $C_1$-$C_{20}$ linear or branched substituted aryl, CN, COOH, COOM, $COOR_7$, $CONHR_7$, CONHOH, or COAA, or $R_4$, $R_5$, and $R_6$ together with B form a heterocyclic ring structure;

where:
M is Li, Na, K, or ammonium ion;
$R_7$ is H, $C_1$-$C_{10}$ alkyl, substituted alkyl, aryl, or substituted aryl; and
AA is $NHCH(R_8)COOR_9$ or $NHCH(R_8)CONHR_9$ wherein $R_8$ is selected from the side chains of common amino acids and $R_9$ is H, or $C_1$-$C_5$ alkyl.

4. A method according to claim 3, wherein X is N.

5. A method according to claim 1, wherein the organic boron compound is characterized by (1) in vivo inhibition of proteolytic enzymes involved in mediating osteoporosis, and (2) in vivo inhibition of prostoglandin sythetase activity.

6. A method according to claim 1, wherein the organic boron compound comprises a boron analog of an α-amino acid.

7. A method according to claim 1, wherein the organic boron compound is selected from the group consisting of carboxyborane adducts of Lewis bases, and their corresponding esters and amides.

8. A method according to claim 1, wherein the organic boron compound comprises a carboxyborane adduct of a Lewis base.

9. A method according to claim 1, wherein the animal subject is a mammalian subject.

10. A method according to claim 1, wherein said organic boron compound is administered as a preventative for osteoporosis.

11. A method according to claim 1, wherein said organic boron compound is administered in treatment of osteoporosis developed in said animal subject.

12. The method according to claim 1, wherein the organic compound is selected from the group consisting of amine carboxyboranes of the formula:

$R_1R_2R_3XBR_4R_5R_6$ wherein:
X is N;
$R_1$, $R_2$, $R_3$, $R_4$, $R_5$ are independently selected from H, $C_1$-$C_{20}$ linear or branched alkyl; and $R_6$ is COOH, and their corresponding metal complexes.

* * * * *